United States Patent
Wang et al.

(10) Patent No.: US 9,090,531 B2
(45) Date of Patent: Jul. 28, 2015

(54) METHOD FOR MITIGATING HCL GENERATION DURING 1,1,2,3-TETRACHLOROPROPENE PURIFICATION

(71) Applicant: Honeywell International Inc., Morristown, NJ (US)

(72) Inventors: Haiyou Wang, Amherst, NY (US); Huseh Sung Tung, Getzville, NY (US); Selma Bektesevic, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 134 days.

(21) Appl. No.: 13/804,738

(22) Filed: Mar. 14, 2013

(65) Prior Publication Data

US 2014/0275660 A1    Sep. 18, 2014

(51) Int. Cl.
  *C07C 17/25* (2006.01)
  *C07C 17/38* (2006.01)
  *C07C 17/383* (2006.01)
  *C07C 17/42* (2006.01)
  *C07C 21/04* (2006.01)
  *C07C 17/278* (2006.01)
  *C07C 17/386* (2006.01)

(52) U.S. Cl.
  CPC .............. *C07C 17/42* (2013.01); *C07C 17/278* (2013.01); *C07C 17/38* (2013.01); *C07C 17/386* (2013.01); *C07C 17/25* (2013.01); *C07C 21/04* (2013.01)

(58) Field of Classification Search
  CPC ...... C07C 17/38; C07C 17/383; C07C 17/25; C07C 21/04
  USPC .................................. 570/262, 227, 238, 226
  See application file for complete search history.

(56) References Cited

U.S. PATENT DOCUMENTS

| 3,092,612 | A | 6/1963 | Makowski | |
|---|---|---|---|---|
| 4,650,914 | A | 3/1987 | Woodard | |
| 5,902,914 | A * | 5/1999 | Rygas et al. | 570/257 |
| 8,058,486 | B2 | 11/2011 | Merkel et al. | |
| 2003/0018225 | A1 | 1/2003 | Klausmeyer | |
| 2003/0028057 | A1 | 2/2003 | Owens et al. | |
| 2009/0216055 | A1* | 8/2009 | Wilson et al. | 570/219 |
| 2010/0181524 | A1 | 7/2010 | Elsheikh et al. | |
| 2011/0196178 | A1* | 8/2011 | Nyberg | 570/160 |
| 2012/0226081 | A1 | 9/2012 | Elsheikh et al. | |
| 2012/0289751 | A1 | 11/2012 | Nose et al. | |

FOREIGN PATENT DOCUMENTS

| EP | 309958 B1 * | 1/1993 |
|---|---|---|
| WO | 2008127940 A1 | 10/2008 |

OTHER PUBLICATIONS

EP0309958B1, Jan. 1993, pp. 1-3; English translation.*
PCT ISR & Written Opinion issued in PCT/US2014/021023 dated Jun. 12, 2014.

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

This invention is directed to a method for mitigating HCl generation during 1230xa purification, which comprises the steps of; (a) adding a chelating agent into 1230xa crude, and (b) conducting the 1230xa purification in the presence of said chelating agent at a quantity sufficient to reduce or prevent 1230xa decomposition. Examples of chelating agent include tributyl phosphate (TBP), tripropyl phosphate (TPP), and triethyl phosphate (TEP). The concentration of chelating agent in 1230xa crude can range from 0.001 to 20 wt %, preferably from 0.01 to 10 wt %, and more preferably from 0.1 to 5 wt %.

11 Claims, No Drawings

METHOD FOR MITIGATING HCL GENERATION DURING 1,1,2,3-TETRACHLOROPROPENE PURIFICATION

FIELD OF INVENTION

The present invention relates to a method for preventing degradation of a chloroalkene, more particularly a chloropropene, and even more particularly a tetrachlorpropene, especially 1,1,2,3-tetrachloropropene (HCO-1230xa) during a purification step.

BACKGROUND OF THE INVENTION

Chlorinated hydrocarbons such as 1,1,2,3-tetrachloropropene (HCO-1230xa) are useful feedstocks for manufacturing refrigerants, blowing agents, biocides, and polymers. For example, 1,1,2,3-tetrachloropropene is useful in the manufacture of herbicide trichloroalkyl diisopropyl thiocarbamate, commonly referred to as "triallate".

More recently, as disclosed in U.S. Pat. No. 8,058,486, 1,1,2,3-tetrachloro-propene (HCO-1230xa) is useful as a starting raw material to produce 2,3,3,3-tetrafluoropropene (HFO-1234yf). HFO-1234yf is a low GWP molecule that can be used as an effective refrigerant, fire extinguishing agent, heat transfer medium, propellant, foaming agent, blowing agent, gaseous dielectric agent, sterilant carrier, polymerization medium, particulate removal fluid, carrier fluid, buffing abrasive agent, displacement drying agent and power cycle working fluid, to name a few. This patent is hereby incorporated herein by reference.

Conventionally, 1,1,2,3-tetrachloropropene (HCO-1230xa) is produced by the dehydrochlorination of 1,1,1,2,3-pentachloropropane (HCC-240 db) either in the presence of a caustic solution or in the presence of Lewis acid catalysts such as $FeCl_3$, and $AlCl_3$.

As disclosed in U.S. Pat. No. 4,650,914, HCC-240 db can be converted, using a caustic solution, into an isomeric mixture of 2,3,3,3-tetrachloropropene and 1,1,2,3-tetrachloropropene. As a final step, the 2,3,3,3-tetrachlorpropene can be isomerized to 1,1,2,3-tetrachloropropene in the presence of a Lewis acid isomerization catalyst such as $FeCl_3$ in a separate reactor. This patent is hereby incorporated herein by reference.

As also disclosed in U.S. Pat. No. 4,650,914, HCC-240 db can be directly converted into 1,1,2,3-tetrachloropropene via a catalytic dehydrochlorination reaction in the presence of a dehydrochlorination catalyst such as $FeCl_3$. During this process, the compound 2,3,3,3-tetrachloropropene is either not formed or it is immediately converted to the 1,1,2,3-tetrachloropropene via an isomerization reaction, catalyzed by the same $FeCl_3$ catalyst.

Applicants have recognized that while Lewis acid catalysts such as $FeCl_3$, and $AlCl_3$ provide advantages over caustic solutions in the conversion of HCC-240 db to HCO-1230xa, the carried over metal ions such as $Fe^{3+}$ and $Al^{3+}$ can cause the HCO-1230xa to decompose and to form HCl during the step of purification such as distillation. The HCl formed in this process can partially dissolve in the desired HCO-1230xa, and as a result, the final HCO-1230xa product will be somewhat acidic, which can complicate its storage and transportation. Thus, there is a need for means by which HCl formation can be mitigated during the HCO-1230xa purification step. This invention provides a solution to this problem.

SUMMARY OF INVENTION

The present invention relates to a method for preventing the degradation of chloropropene compounds during purification. In one embodiment, the method comprises the steps of (a) providing a crude chloropropene composition containing at least one metal ion, (b) adding to said chloropropene composition an effective amount of at least one chelating agent, and (c) purifying the chloropropene composition by a purification technique such as distillation in the presence of said chelating agent to retard or prevent the decomposition of the chloropropene compounds.

One embodiment of this invention is directed to method for preventing the degradation of HCO-1230xa during its purification, which comprises the following steps:

(a) adding a chelating agent to a crude composition comprising HCO-1230xa, and (b) conducting the HCO-1230xa purification in the presence of said chelating agent at an quantity sufficient to reduce or eliminate HCO-1230xa decomposition.

In a preferred embodiment, this invention can be described as a new method for preventing the degradation of HCO-1230xa during its purification, which comprises the following steps:

(1) providing a crude composition comprising HCO-1230xa, wherein the crude composition includes at least HCO-1230xa and one or more metal ions such as $Fe^{3+}$ and $Al^{3+}$, (2) adding an effective amount of at least one chelating agent to the crude HCO-1230xa composition, (3) purifying the crude HCO-1230xa composition by employing one or more purification techniques, such as distillation, in the presence of said chelating agent to prevent the decomposition of the HCO-1230xa in the composition.

The chelating agent preferably comprises a trialkyl phosphate compound with a generic formula of $R_3PO_4$, wherein R is a $C_1$-$C_6$ alkyl (e.g. $C_1$, $C_2$, $C_3$, $C_4$, $C_5$, $C_6$ alkyl and combinations and permutations of any thereof). In one embodiment, R is a $C_2$-$C_4$ alkyl. In another embodiment, R is a $C_4$ alkyl (butyl).

The term "alkyl" as used herein includes cyclic or acyclic and straight-chain or branched alkyl groups, such as, methyl, ethyl, n-propyl, i-propyl, or the different isomers thereof. In certain embodiments, R is a straight-chain or branched alkyl.

In certain embodiments, preferred trialkyl phosphates include tributyl phosphate (TBP), tripropyl phosphate (TPP), and triethyl phosphate (TEP). The concentration of chelating agent in 1230xa crude can be ranged from 0.001 to 20 wt %, preferably from 0.01 to 10 wt %, and more preferably from 0.1 to 5 wt %.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, 1,1,2,3-tetrachloropropene (HCO-1230xa) is a useful raw material for producing 2,3,3,3-tetrafluoropropene (HFO-1234yf), a low GWP molecule. Depending on different manufacturing processes, the HCO-1230xa crude may contain different levels of metal ions such as iron ions. During the purification step these metal ions can serve as a dehydrochlorination catalyst, and cause the HCO-1230xa to decompose, forming HCl. The formed HCl can also partially dissolved in HCO-1230xa, causing corrosion of storage tanks and process lines and equipment. Thus, there is a need for means by which HCl formation during the purification of HCO-1230xa can be mitigated.

In one embodiment, the present invention relates to a method for preventing the degradation of a chloropropene, which method comprises (a) providing a crude chloropropene composition containing at least one metal ion, (b) adding to said crude chloropropene composition an effective amount of at least one chelating agent, and (c) conducting a purification technique, such as distillation, in the presence of said chelating agent to retard or prevent the decomposition of the chloropropene.

Without limitation herein, chloropropene compounds especially include chloropropenes such as for example, tetrachloropropenes, such as 1,1,2,3-tetrachloro-propene, 2,3,3,3-tetrachloropropene, 1,1,3,3-tetrachloro-propene, 1,3,3,3-tetrachloro-propene, 1,2,3,3-tetrachloropropene; trichloropropenes, such as 1,1,3-trichloro-propene. Combinations of various chloropropenes, including the foregoing, are encompassed by the term, as are all cis and trans isomers of the same.

In one embodiment, the chloropropene is a tetrachloropene. In another embodiment the chloropropene is 1,1,2,3-tetrachloropropene (1230xa). In another embodiment, the chloropropene of this invention includes one or more chlorinated compounds selected from Formula I or II or combinations thereof:

1) $CX_2=CCl-CH_2X$ (Formula I)

2) $CX_3-CCl=CH_2$ (Formula II)

wherein X is independently selected from fluorine (F), chlorine (Cl), bromine (Br) and iodine (I), provided that at least one of X is not F.

Without limitation herein, metal ions contained in chloropropenes are selected from the group consisting of $Fe^{3+}$, $Al^{3+}$, $La^{3+}$, $Cr^{3+}$, $Ni^{2+}$, $Cu^{2+}$, and their combinations. The metal ions can be either from carried over Lewis acid catalysts or from the dissolution of the surface layer of a storage container or a reaction vessel, or from any other source (e.g., contamination).

Without limitation herein, the chelating agent is a trialkyl phosphate with a generic formula of $R_3PO_4$, wherein R is a $C_1$-$C_6$ alkyl (e.g. $C_1$, $C_2$, $C_3$, $C_4$, $C_5$, $C_6$ alkyl and combinations and permutations of any thereof). In one embodiment, R is a $C_2$-$C_4$ alkyl. In another embodiment, R is a $C_4$ alkyl (butyl). The term "alkyl" as used herein includes cyclic or acyclic and straight-chain or branched alkyl groups, such as, methyl, ethyl, n-propyl, i-propyl, or the different isomers thereof. In certain embodiments, R is a straight-chain or branched alkyl. In certain preferred embodiments, preferred trialkyl phosphates include tributyl phosphate (TBP), tripropyl phosphate (TPP), and triethyl phosphate (TEP). The trialkyl phosphate compound can be added to the crude chloropropene by methods known in the art.

The phrase "effective amount" is that amount of chelating agent that either prevents decomposition and/or other forms of degradation in the chloropropene, including the formation of undesirable components such as acids, e.g., HCl, oxidation by-products, oligomers, and the like; or inhibits such decomposition to a point whereby such undesirable components are present in amounts immaterial to further processing, e.g., they do not need to be removed or they do not have any meaningful affect on operations or processing, e.g., in processes to prepare 2-chloro-3,3,3-trifluoropropene (1233xf) and/or 2,3,3,3-tetrafluoroprop-1-ene (1234yf). The concentration of chelating agent in a chloropropene crude composition such as 1230xa crude can be ranged from 0.001 to 20 wt %, preferably from 0.01 to 10 wt %, and more preferably from 0.1 to 5 wt %.

In a later step of the process, the present invention provides for the purification of the crude product by distillation. Fractional vacuum distillation is carried out at about 5 mm Hg to about 200 mm Hg and a temperature of from about 50° C. to about 150° C. to recover the product. It has been discovered that when this purification step is carried out in the presence of a trialkyl phosphate such as tributyl phosphate or other metal chelating compound, the distillation yield of purified product is significantly improved. While not wishing to be bound by particular theory, it is believed that trialkyl phosphate forms complexes with metal ions present in 1230xa crude and consequently deactivates metal ions as catalysts for 1230xa decomposition reactions such as dehydrochlorination reaction.

EXAMPLE 1

700.0 g of 1230xa crude containing 100 ppm of $Fe^{3+}$ is charged to a 1000 ml round bottom flask in a vacuum distillation apparatus. 10.0 g tributyl phosphate (TBP) is added. The charged material is distilled under 0.5 psia at 69-70° C. The distillation is stopped when the reboiler flask is almost empty and no more droplets of distillate are observed. The residual material is brown in color without the presence of tars. The distillate weighs 684.2 g, 97.74% of the starting weight. The acid-base titration shows the distillate contains less than 10 ppm of HCl.

COMPARATIVE EXAMPLE 1

700.0 g of 1230xa crude containing 100 ppm of $Fe^{3+}$ is charged to a 1000 ml round bottom flask in a vacuum distillation apparatus. No tributyl phosphate (TBP) is added. The material is distilled under 0.5 psia at 69-70° C. The distillation is stopped when beginning decomposition of the reboiler material is observed. The residual material in the reboiler flask becomes tarry and the distilled material dropping from the condenser turns brown. The distillate weighs 623.2 g, 89.03% of the starting weight. Weight accountability of the distillation was 96.74%. The acid-base titration shows the distillate contains about 200 ppm of HCl.

Example 1 and Comparative Example 1 illustrate that the use of a metal chelating compound provides improved distillation yields and prevents the decomposition of product and tar formation.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for preventing the degradation of 1230xa during its purification, which comprises the following steps:
   (a) providing a crude composition comprising 1230xa and one or more Lewis Acid metal ions selected from the group consisting of $Fe^{3+}$, $Al^{3+}$, $La^{3+}$, $Cr^{3+}$, $Ni^{2+}$, $Cu^{2+}$, and combinations thereof;
   (b) adding at least one chelating agent to the crude composition, wherein the chelating agent comprises a trialkyl phosphate with a generic formula of $R_3PO_4$, wherein R is selected from the group consisting of $C_1$, $C_2$, $C_3$, $C_4$, $C_5$, $C_6$ alkyl and combinations thereof; and
   (c) purifying the crude composition by distillation in the presence of the chelating agent to thereby prevent 1230xa decomposition.

2. The method of claim 1, wherein R comprises a $C_2$-$C_4$ alkyl group.

3. The method of claim 2, wherein R is a $C_4$ alkyl.

4. The method of claim 1, wherein the alkyl group is selected from the group consisting of cyclic, straight-chain and branched alkyl groups.

5. The method of claim 1, wherein the alkyl group is selected from the group consisting of methyl, ethyl, n-propyl, and i-propyl.

6. The method of claim 1, wherein the R group is either a straight-chain or a branched alkyl group.

7. The method of claim 1, wherein the chelating agent comprises one or more trialkyl phosphate compounds.

8. The method of claim 7, wherein the trialkyl phosphate compounds are selected from the group consisting of tributyl phosphate (TBP), tripropyl phosphate (TPP), triethyl phosphate (TEP), and mixtures thereof.

9. The method of claim 1, wherein the concentration of the chelating agent in the crude composition ranges from about 0.001 to 20 wt %.

10. The method of claim 1, wherein the concentration of the chelating agent in the crude composition ranges from about 0.01 to 10 wt %.

11. The method of claim 1, wherein the concentration of the chelating agent in the crude composition ranges from about 0.1 to 5 wt %.

* * * * *